United States Patent [19]
Grözinger et al.

[11] Patent Number: 5,431,641
[45] Date of Patent: Jul. 11, 1995

[54] PLUG ARRANGEMENT FOR CONNECTING STERILE AND NON-STERILE APPARATUS

[75] Inventors: Reiner Grözinger, Alling; Roland Buck-Braunwarth, Frichingen; Gerhard Buess, Tübingen, all of Germany

[73] Assignee: Dornier Medizintechnik GmbH, Germany

[21] Appl. No.: 251,682

[22] Filed: May 31, 1994

[30] Foreign Application Priority Data

Jun. 2, 1993 [DE] Germany .................. 43 18 325.5

[51] Int. Cl.⁶ ............................................. A61M 25/00
[52] U.S. Cl. ................................. 604/283; 604/905; 141/329
[58] Field of Search ............... 604/283, 411, 414, 905; 141/311, 312, 329, 332, 333, 367, 368, 369

[56] References Cited

U.S. PATENT DOCUMENTS

| | | | |
|---|---|---|---|
| 5,086,813 | 2/1992 | Galloway | 604/905 X |
| 5,199,473 | 4/1993 | Galloway | 604/411 X |
| 5,370,164 | 12/1994 | Galloway | 141/329 |

*Primary Examiner*—John D. Yasko
*Attorney, Agent, or Firm*—Evenson, McKeown, Edwards & Lenahan

[57] ABSTRACT

A plug-type connection is used for connecting at least one sterile electrical, optical and/or fluid-carrying line to at least one non-sterile apparatus with one line-side and one equipment-side plug unit respectively. The equipment-side plug unit is surrounded by at least one sterile foil which is clamped tightly between respective corresponding sealing and clamping edges of the line-side and the equipment-side plug units which surround the line to be plugged in. The line-side and/or equipment-side plug unit has a cutting device to cut the foil in the area of the lines to be contacted.

16 Claims, 4 Drawing Sheets

PLUG ARRANGEMENT FOR CONNECTING STERILE AND NON-STERILE APPARATUS

BACKGROUND AND SUMMARY OF THE INVENTION

This invention relates to a plug-type connection for connecting at least one sterile electrical, optical and/or fluid-carrying line to at least one non-sterile device, with one plug unit on the line side, and one on the equipment side.

In the different surgical applications, it is necessary to establish within the sterile operating area plug-type connections between connecting lines from the patient to the technical supply devices and vice versa. Particularly in the case of minimally invasive surgery, several different auxiliary devices are required for the preparation of the operating field and the surgical procedure itself, for which connections must be established by means of hoses and cables.

German Patent Document P 42 42 069.5 discloses a workplace system in which the connecting lines are guided to the patient by a central connection field which is situated within the sterile operating area. The connection of the connecting lines to the connection field is provided by means of one or several multiple plug-type connections, so that there is no contact with the sterile equipment components in the sterile operating area and the sterile operating personnel. To maintain its sterility, this sterile connection field is covered by the assisting personnel with a sterile covering (hose-type bag) before it is swivelled into the sterile operating area. After the connection field is in place in the sterile operating area, the sterile connecting lines and plugs must be connected to the central connection field by sterile operating personnel while the sterility is maintained. To connect the multiple plug-type connections, it is necessary to cut fitting openings out of the sterile covering in the connection area.

It is an object of the present invention to provide a plug-type connection that is easy to handle different types of connecting lines, and that makes it possible to connect these lines under sterile conditions within the sterile operating field to non-sterile equipment, without exposure of non-sterile surfaces are exposed during the connecting process.

This object is achieved by the plug arrangement constructed according to the invention in which sterile and non-sterile parts remain hermetically separated from one another, particularly during the connection process (which can easily be carried out by hand). The non-sterile equipment-side plug unit, including the lines connected to it which extend into the sterile operating area and are to be contacted (possibly also the apparatus itself) are surrounded by a sterile foil. Before its insertion into the equipment-side plug unit, the plug unit which is situated in the sterile operating area and has lines leading to the patient, cooperates with the equipment-side plug unit to seal-off the contact area by clamping the foil between respective corresponding sealing and clamping edges of the two plug units. Subsequently, an opening is cut in the foil of the plug area to permit the connection. The cut-out foil is removed into the interior of the plug so that then the connection can be carried out between the lines to be contacted and the plug-type connection as a whole can be locked.

All functional parts of the cutting device as well as the individual plug elements of the lines to be connected are situated within the closed, preferably circular sealing lip so that, after the penetration of the foil, no open connection exists from the non-sterile equipment-side plug unit to the sterile line-side plug area. In addition, this sealing also protects the interior plug area from contaminations from the outside.

Other objects, advantages and novel features of the present invention will become apparent from the following detailed description of the invention when considered in conjunction with the accompanying drawings.

DETAILED DESCRIPTION OF THE DRAWINGS

Figure 1A:
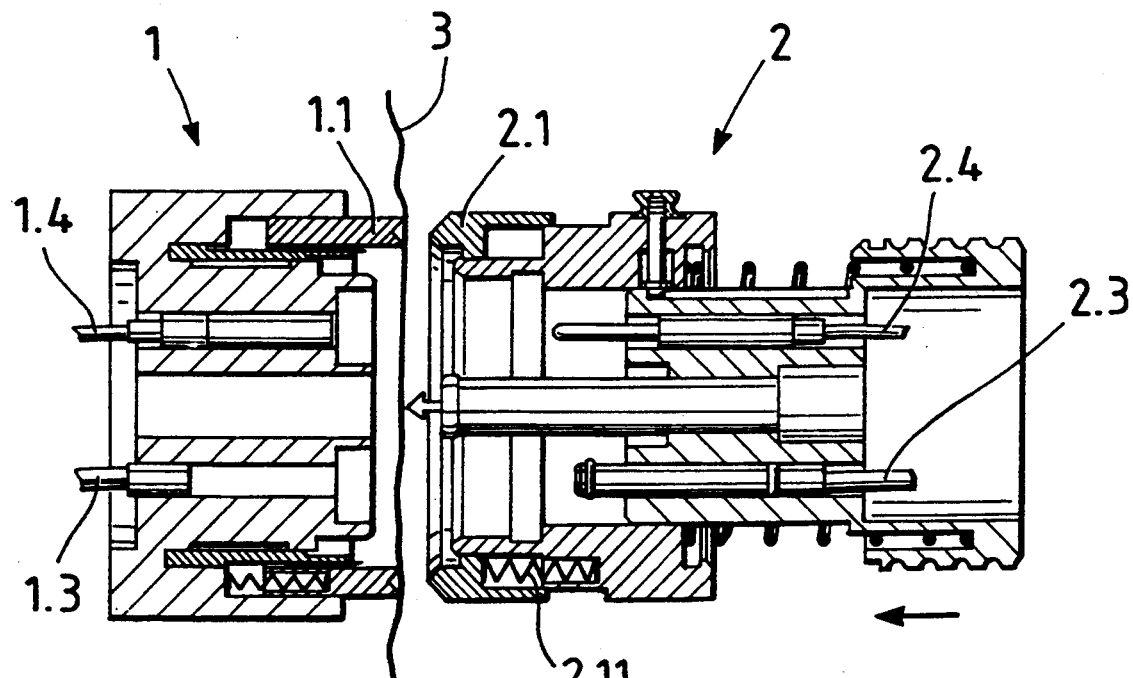
FIGS. 1a to 1d are cross-sectional views of a plug-type connection in four phases of the plug-in process.

The embodiment illustrated in FIGS. 1a to 1d has an equipment-side non-sterile plug unit 1 and a line-side sterile plug unit 2. The sterile plug unit 2 has three telescoping sections, including a sealing and clamping ring 2.1 (discussed below), a center part 2.2 and a plug element 2.7. During the insertion process, these three parts, which are spring biased in an extended position, are collapsed into one another consecutively. That is, the center part 2.2 first collapses into the sealing and clamping ring 2.1, and the plug element 2.7 then collapses into the center part 2.2, as described in detail below.

Before the plug-in process, the two plug parts are separated from one another by a sterile foil 3, which, in an additional area (not shown), also serves to separate the non-sterile equipment part projecting into the operating area from the sterile area of the operating field. The two plug parts 1 and 2 each have elastically disposed sealing and clamping rings 1.1 and 2.1 which fit on one another and surround the contact field of the lines 1.3, 1.4 and 2.3, 2.4 to be connected. In the embodiment shown, the line 1.3, 2.3 is a fluid-carrying line (for example, an intake line connected with a vacuum pump), and line 1.4, 2.4 is an insulated electrical contact line. However, whether and in which manner the different types of lines are combined in a plug as well as their number depends particularly on safety-related considerations.

Figure 1B:
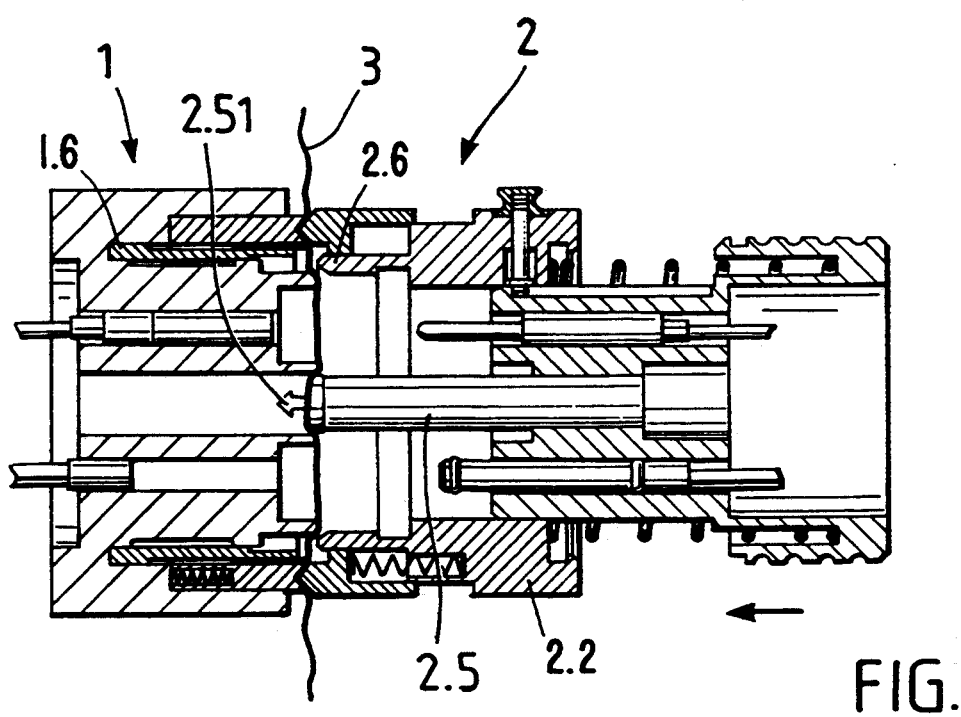
Figure 1C:
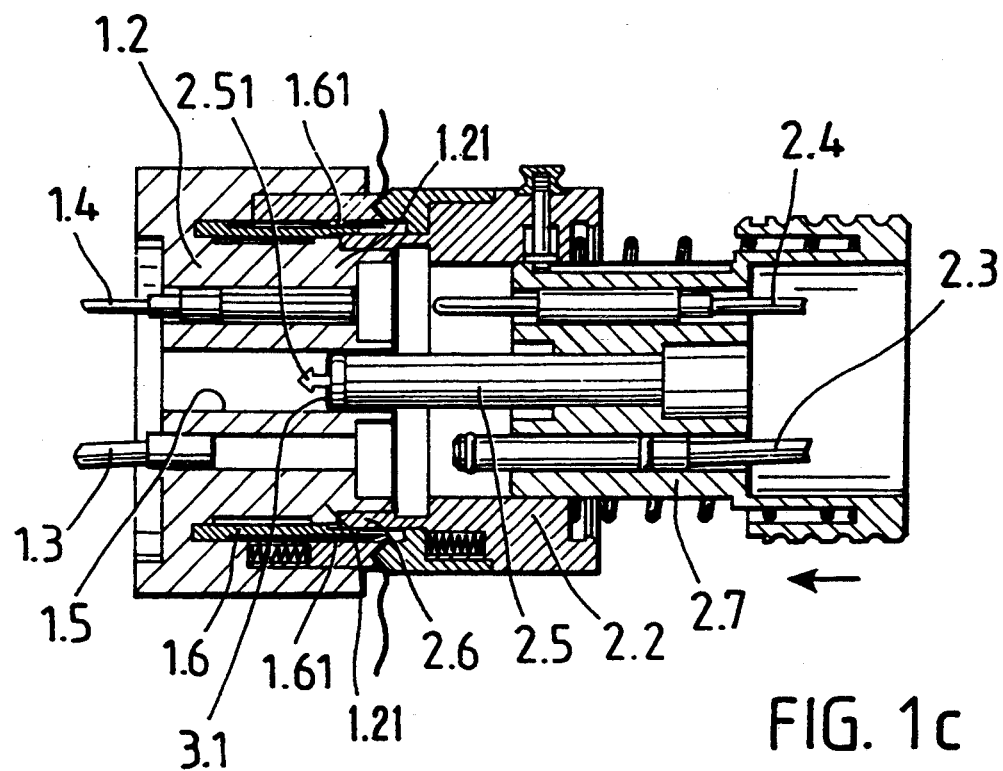

At the time of the initial contact of the two plug parts 1 and 2 illustrated in FIG. 1b, the foil 3 is clamped between the sealing and clamping rings 1.1 and 2.1 and is pierced by a mandrel extension 2.51 arranged at the tip of a ram 2.5 in the center of the plug unit 2. When the plug unit 2 is pushed in farther, as shown in FIG. 1c, the center part 2.2 of the plug unit 2 collapses into the sealing and clamping ring 2.1, and the foil 3, which was previously clamped and tensioned, is further tensioned by a ring 2.6 disposed concentrically with respect to the sealing and clamping ring 2.1 and is pressed against a cutting ring 1.6 which is concentric to the sealing and clamping ring 1.1 and is equipped with blades 1.61 (see FIG. 1c) projecting axially at the periphery of the open end thereof which contacts the foil 3. When a the spring-deflected sealing and clamping ring 1.1 reaches a stop 1.21 on the plug part 1, it triggers a conventional microswitch (FIG. 1e), and activates an electric drive (not shown) which rotates the cutting ring 1.6, so that the blades 1.61 cut the area situated within the sealing and clamping edges 1.1 and 2.1 out of the foil. The ram 2.5 presses the cutout foil piece 3.1 into a central bore 1.5 of the plug part 1, thereby pulling it out of the actual contact field.

Figure 1D:
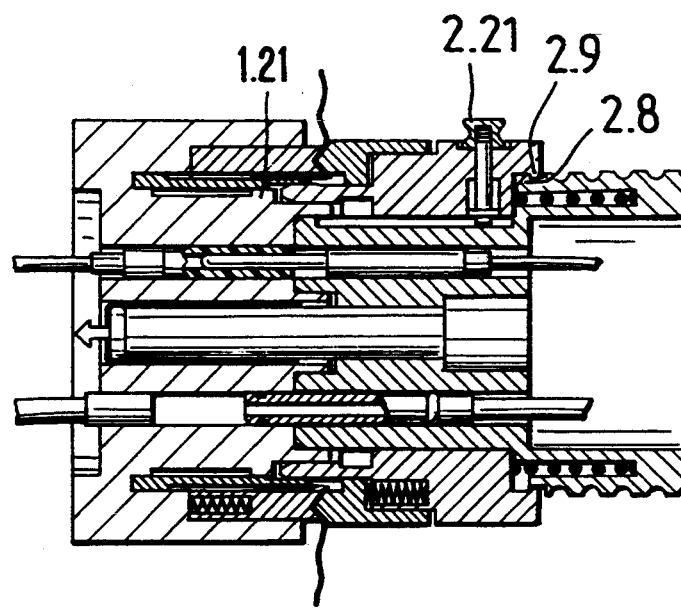
Figure 1E:
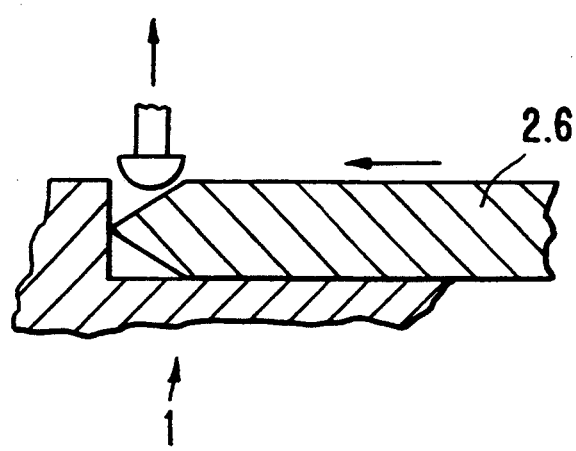
FIG. 1e is a schematic view of a mechanically actuated microswitch for actuating a drive motor for the cutting ring of FIGS. 1a–1d.

In this phase of the plug-in process, the center part 2.2 of the plug unit 2 is disposed in the center piece 1.2 of the plug part 1 in a flush and clearly positioned manner. The plug element 2.7 of the plug unit 2 which carries the contacts 2.3 and 2.4 to be plugged in is axially displaceable in a guide of the plug element 2.2, and in the further course of the plug-in process is pushed against the center piece 1.2 of the plug part 1, so that the lines to be plugged in are connected (FIG. 1d). At the end of the plug-in process, a locking device 2.8 on the plug element 2.7 locks into a corresponding groove 2.9 of the plug element 2.2 which, in turn, is fixedly connected with the equipment-side plug part 1 and 1.2 by means of a bayonet locking arrangement.

To disconnect the plug-type connection, the lock 2.8 is released; the plug element 2.7 is then pulled back; and the bayonet lock of the plug element 2.2 is rotated and disconnected from the plug part 1. The foil piece 3.1 hanging on the mandrel extension 2.51 is pulled out of the opening 105 and can therefore be removed.

For the purpose of sterilization, the plug part 2 can be further disassembled into the elements 2.2 and 2.7 by lifting a locking pin 2.21 and pulling the plug element 2.7 out of the guide of the plug element 2.2. The sealing and clamping ring 2.1 held by means of the spring 2.11 can then also be withdrawn.

The fastening of the plug-in contacts 1.3, 1.4 and 2.3, 2.4 in the respective plug elements 1 and 2 is designed so that, in the case of disturbances, the individual connections may be changed under sterile conditions, in that these are in each case pulled off on the rear of the plug and are replaced by new plug-in contacts. As long as such a change of contacts does not occur at the same time on both plug parts 1 and 2, the separation between the non-sterile and the sterile area will be maintained.

Instead of the cutting ring 1.6 equipped with blades 1.61, as an alternative, a circular heating wire may be installed to cut the foil out of the contact area by briefly heating it during the plug-in process.

Instead of the ram 2.5 illustrated in the embodiment, a suction device may also be used to remove the foil by way of the duct 1.5. In this case, a transparent ductile material of a thickness of between 50 and 100 μm can be used as the foil.

Figure 2:
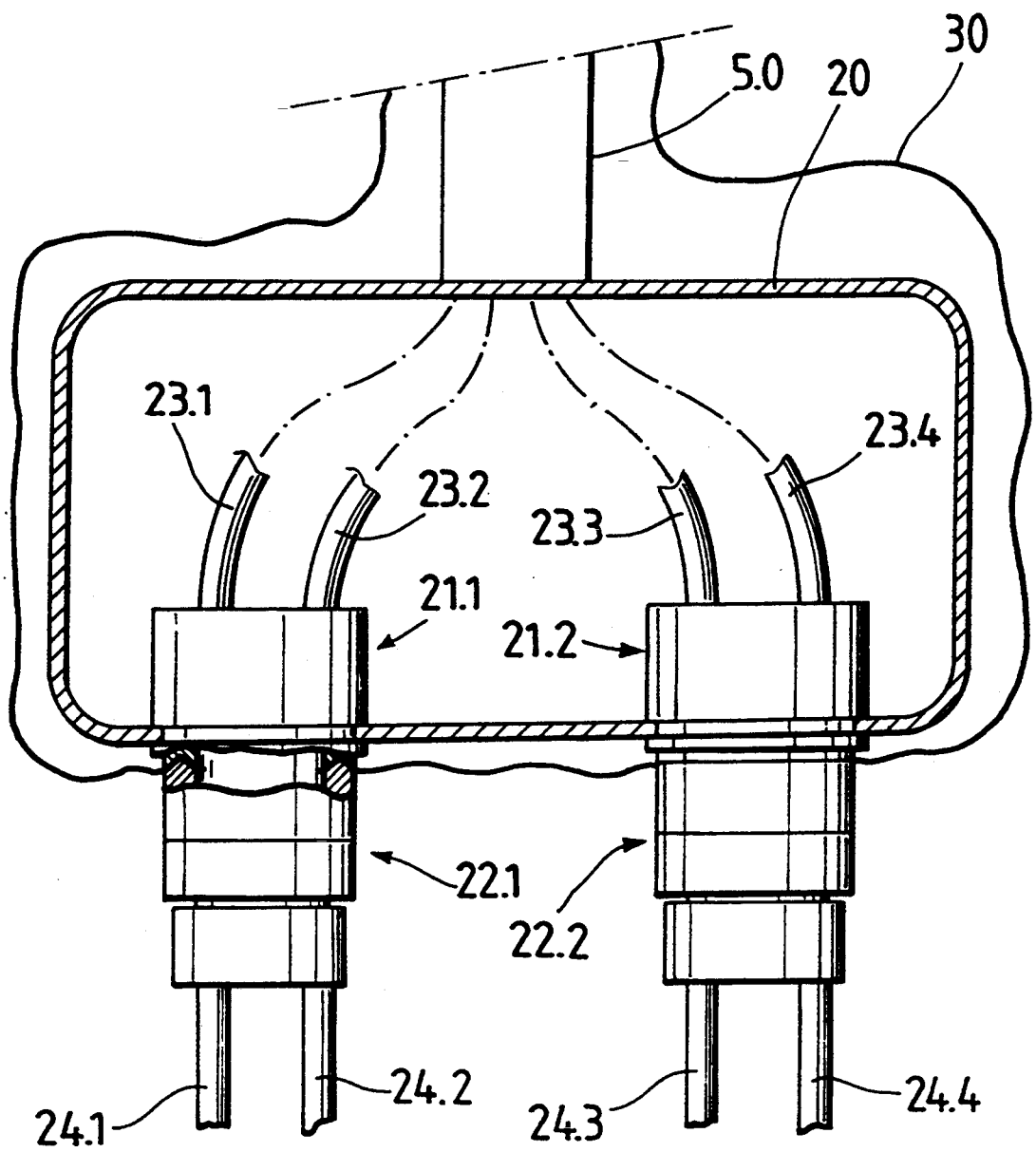
FIG. 2 is a view of a connection field with several sterile plug-type connections.

In the embodiment illustrated in FIG. 2, two equipment-side plug units 21.1, 21.2 constructed according to FIG. 1 are arranged on a connection field, with the respective lines 23.1 to 23.4 to be plugged in guided by way of a shaft 5.0 to the equipment situated in the non-sterile area. The connection field including the shaft 5.0 is surrounded by a foil bag 30 which separates the sterile and non-sterile areas.

Corresponding plug parts 22.1 and 22.2 can be connected to the plug parts 21.1 and 21.2 arranged in the connection field, in the construction described in FIG. 1. The lines 24.1, 24.2, 24.3 and 24.4 arranged on these plug parts 22.1 and 22.2 lead to the sterile operating field.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. Apparatus for connecting at least one sterile line to at least one non-sterile line connected to non-sterile equipment, said apparatus comprising:

a first plug unit having first connecting elements coupled to said at least one non-sterile line and having a first sealing and clamping edge which surrounds said first connecting elements;

at least one sterile foil surrounding at least said first plug unit;

a second plug unit having second connecting elements coupled to said at least one sterile line, and having a second sealing and clamping edge which surrounds said second connecting elements, said second sealing and clamping edge being configured to cooperate with said first sealing and clamping edge to clamp and seal a portion of said sterile foil which separates said first connecting elements from said second connecting elements; and a cutting device for cutting said portion of said sterile foil which separates said first and second connecting element.

2. Apparatus according to claim 1 wherein:

said first plug unit has a first elastically disposed ring which comprises said first sealing and clamping edge; and said second plug unit has a second elastically disposed ring which comprises said second sealing and clamping edge.

3. Apparatus according to claim 1 wherein said cutting device is arranged to cut out said portion of said sterile foil which separates said first and second connecting elements.

4. Apparatus according to claim 2 wherein said cutting device is arranged to cut out said portion of said sterile foil which separates said first and second connecting elements.

5. Apparatus according to claim 3 wherein said cutting device is arranged on said first plug unit and said cut out portion of the sterile foil comprises a circular area within said first sealing and clamping edge.

6. Apparatus according to claim 5 wherein said cutting device comprises a drive unit which is activated by convergence of said first and second plug units.

7. Apparatus according to claim 1 wherein the cutting device comprises a heating wire which extends along an interior side of the first sealing and clamping edge.

8. Apparatus according to claim 6 wherein the cutting device comprises a heating wire which extends along an interior side of the first sealing and clamping edge.

9. Apparatus according to claim 6 wherein the cutting device further comprises a punching device which extends along the interior side of said sealing and clamping edge.

10. Apparatus according to claim 1 further comprising means for removing the foil cutout from between said first and second plug units before connection of the sterile and non-sterile lines.

11. Apparatus according to claim 10 wherein said means for removing comprises one of: a suction device, a blowing device and a pushing device.

12. Apparatus according to claim 1 wherein the second plug unit comprises an interior part having said second connecting elements, and a coupling part, which is axially displaceable with respect to the interior part and has a sealing and clamping edge.

13. Apparatus according to claim 10 wherein the second plug unit comprises an interior part having said second connecting elements, and a coupling part, which is axially displaceable with respect to the interior part and has a sealing and clamping edge.

14. Apparatus according to claim 1 wherein the sterile foil has a thickness of between 50 μm and 100 μm and consists of a smooth ductile material.

15. Apparatus according to claim 1 wherein a plurality of first plug units are arranged on a connection field and are surrounded by a closed foil.

16. Apparatus according to claim 1 wherein the sterile and non-sterile lines can be disconnected from the respective first and second plug parts.

* * * * *